(12) United States Patent
Lyden et al.

(10) Patent No.: US 8,694,095 B2
(45) Date of Patent: Apr. 8, 2014

(54) CONFIGURATION OF PACING OUTPUT CHANNELS

(75) Inventors: Michael J. Lyden, Shoreview, MN (US); Nicholas J. Stessman, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1504 days.

(21) Appl. No.: 12/328,603

(22) Filed: Dec. 4, 2008

(65) Prior Publication Data

US 2009/0149905 A1 Jun. 11, 2009

Related U.S. Application Data

(60) Provisional application No. 61/009,747, filed on Dec. 30, 2007, provisional application No. 61/005,568, filed on Dec. 5, 2007.

(51) Int. Cl.
*A61N 1/00* (2006.01)

(52) U.S. Cl.
USPC .................................................. 607/9

(58) Field of Classification Search
USPC ...................................... 607/9, 13
See application file for complete search history.

(56) References Cited

U.S. PATENT DOCUMENTS

| 3,517,663 A | 6/1970 | Bowers et al. |
| 4,114,627 A * | 9/1978 | Lewyn et al. ............ 607/13 |
| 5,109,848 A | 5/1992 | Thomas et al. |
| 5,843,136 A * | 12/1998 | Zhu et al. ............ 607/13 |
| 5,941,903 A | 8/1999 | Zhu et al. |
| 6,226,551 B1 | 5/2001 | Zhu et al. |
| 6,427,085 B1 | 7/2002 | Boon et al. |
| 2001/0031990 A1 | 10/2001 | Zhang et al. |
| 2005/0245970 A1 | 11/2005 | Erickson et al. |

FOREIGN PATENT DOCUMENTS

| EP | 0308536 A1 | 3/1989 |
| JP | 5654860 A | 5/1981 |
| JP | 1101980 A | 4/1989 |
| JP | 2002516732 A | 6/2002 |
| WO | WO-01/74441 A2 | 10/2001 |
| WO | WO-2009/075763 A2 | 6/2009 |
| WO | WO-2009075763 A3 | 4/2010 |

OTHER PUBLICATIONS

"International Application Serial No. PCT/US2008/013355, International Search Report mailed Feb. 24, 2010", 6 pgs.
"International Application Serial No. PCT/US2008/013355, Written Opinion mailed Feb. 26, 2010", 10 pgs.

(Continued)

*Primary Examiner* — Christopher D Koharski
*Assistant Examiner* — Nadia Ahmad
(74) *Attorney, Agent, or Firm* — Schwegman Lundberg & Woessner, P.A.

(57) ABSTRACT

During auto-threshold, autocapture, or other evoked response sensing, post-pace artifact is reduced by using a smaller coupling capacitor value than what is used when not in such an evoked response sensing configuration. This can be accomplished by borrowing another capacitor for use as the coupling capacitor. The borrowed capacitor can be a backup pacing capacitor from the same or a different pacing channel. The borrowed capacitor can also be a coupling capacitor from a different pacing channel.

10 Claims, 4 Drawing Sheets

(56) References Cited

OTHER PUBLICATIONS

"Application Serial No. PCT/US2008/013355, Invitation to Pay Additional Fees and Partial International Search Report mailed on May 28, 2009", 8 pgs.

"European Application Serial No. 08860759.3, Official Action mailed Jul. 15, 2010", 1 pg.

"European Application Serial No. 08860759.3, Response filed Aug. 16, 2010 to Official Action mailed Jul. 15, 2010", 14 pgs.

"European Application Serial No. 10174252.6, Extended European Search Report mailed Dec. 16, 2010", 4 pgs.

"European Application Seriai No. 10174252.6, Response flied Jul. 13 2011 to European Search Report dated Dec. 16, 2010", 1 pg.

"Japanese Application Serial No. 2010-536929, Office Action mailed Apr. 17, 2012", With English Translation, 12 pgs.

"Japanese Application Serial No. 2010-536929, Response filed Sep. 18, 2012 to Office Action mailed Apr. 17, 2012", With English Claims, 9 pgs.

\* cited by examiner

CONFIGURATION OF PACING OUTPUT CHANNELS

CROSS-REFERENCE TO RELATED APPLICATIONS

This application claims the benefit under 35 U.S.C. 119(e) of U.S. Provisional Application No. 61/005,568, filed on Dec. 5, 2007, and of U.S. Provisional Application No. 61/009,747, filed on Dec. 30, 2007, each of which are hereby incorporated by reference in their entirety.

TECHNICAL FIELD

This patent document pertains generally to the field of cardiac rhythm management devices, including, among other things, atrial, ventricular, and dual chamber pacemakers.

BACKGROUND

A cardiac rhythm management device can electrostimulate excitable heart tissue cells adjacent to the electrode of the lead coupled to the rhythm management device. Response to myocardial stimulation or "capture" is a function of the positive and negative charges found in each myocardial cell within the heart. A cardiac rhythm management device causes a depolarization or evokes a response when the energy of the pacing or other electrostimulus delivered to the myocardium exceeds a threshold value. This threshold value, referred to as the capture threshold, represents the amount of electrical energy that will alter the permeability of the myocardial cells to thereby initiate cell depolarization. If the energy of the pacing stimulus does not exceed the capture threshold, then the permeability of the myocardial cells will not be altered and thus no depolarization can result. If, on the other hand, the energy of the pacing stimulus exceeds the capture threshold, then the permeability of the myocardial cells will be altered such that depolarization can result.

Overview

Example 1 describes an apparatus. In this example, the apparatus can include an implantable medical device. The implantable medical device can include first electrostimulation voltage generator, configured to generate a first electrostimulation voltage. A first capacitor can be coupled to the first electrostimulation voltage generator, and configured to be capable of storing the first electrostimulation voltage. A second capacitor can comprise a capacitance value that is configurable between different at least first and second capacitance values. A processor can comprise an evoked-response sensing mode. The processor can be configured to place the second capacitor in series with the first capacitor during delivery of the first electrostimulation voltage to an electrostimulation target, such that the first capacitance value is used during the delivery when in an evoked-response sensing mode and the second capacitance value is used during the delivery when not in an evoked-response sensing mode.

In Example 2, the apparatus of Example 1 can optionally be configured such that the evoked-response sensing mode comprises at least one of an autocapture mode or an autothreshold mode. The processor can be configured to re-configure the second capacitor from the second capacitance value to the first capacitance value when the evoked-response sensing mode is enabled, wherein the second capacitance value exceeds the first capacitance value.

In Example 3, the apparatus of any one or more of Examples 1-2 can optionally be configured such that the processor is configured to re-configure the second capacitor value from the second capacitance value to the first capacitance value by placing capacitors in series to provide the first capacitance value of the second capacitor.

In Example 4, the apparatus of any one or more of Examples 1-3 can optionally be configured such that the processor is configured to re-configure the second capacitor from the second capacitance value to the first capacitance value by substituting a different capacitor when the evoked-response sensing mode is enabled.

In Example 5, the apparatus of any one or more of Examples 1-4 can optionally be configured such that the processor can be configured to re-configure the second capacitor value from the second capacitance value to the first capacitance value by substituting a same-channel back-up pacing supply capacitor from the same pacing channel when the evoked-response sensing mode is enabled.

In Example 6, the apparatus of any one or more of Examples 1-5 can optionally be configured such that the processor can be configured to re-configure the second capacitor from the second capacitance value to the first capacitance value by borrowing a different capacitor from a different pacing channel when the evoked-response sensing mode is enabled.

Example 7 describes a method. In this example, the method can comprise generating a first electrostimulation voltage, storing the first electrostimulation voltage on a first capacitor, delivering the first electrostimulation voltage from the first capacitor to an electrostimulation target through a second capacitor in series with the first capacitor, enabling an evoked-response sensing mode, and decreasing a capacitance value of the second capacitor during the delivering in response to enabling the evoked-response sensing mode.

In Example 8, the method of Example 7 can optionally be performed such that decreasing the capacitance value of the second capacitor comprises using a back-up pacing capacitor during the evoked-response sensing mode.

In Example 9, the method of any one or more of Examples 7-8 can optionally be performed such that using a back-up pacing capacitor during the evoked-response sensing mode comprises borrowing a back-up pacing supply capacitor from another pacing channel during the evoked response sensing mode.

In Example 10, the method of any one or more of Examples 7-9 can optionally be performed such that decreasing the capacitance value of the second capacitor comprises using a series combination of capacitors for the second capacitor during the evoked-response sensing mode.

Example 11 describes an apparatus. In this example, the apparatus can comprise an implantable medical device. The implantable medical device can comprise a first electrostimulation energy delivery channel. The first electrostimulation energy delivery channel can comprise a first electrostimulation voltage generator, configured to generate a first electrostimulation voltage. The first electrostimulation energy delivery channel can also comprise a first capacitor, coupled to the first electrostimulation voltage generator, and configured to be capable of storing the first electrostimulation voltage. The first electrostimulation energy delivery channel can also comprise a first switching circuit, coupled to the first capacitor, configured to facilitate delivery of the first electrostimulation voltage from the first capacitor to a target. The implantable medical device can also comprise a second electrostimulation energy delivery channel. The second electrostimulation energy delivery channel can comprise a second electrostimulation voltage generator, configured to generate a second electrostimulation voltage. The second electrostimulation energy delivery channel can comprise a second capacitor, coupled to the second electrostimulation voltage generator, and configured to be capable of storing the second electrostimulation voltage. The second electrostimulation energy delivery channel can also comprise a second switching circuit, coupled to the second capacitor, configured to facilitate delivery of the second electrostimulation voltage from the second capacitor to a target. The second electrostimulation energy delivery channel can also comprise a processor, configured to control configuration of the second capacitor to be in series with the first capacitor during delivery of the first electrostimulation voltage from the first capacitor to the target.

In Example 12, the apparatus of Example 11 can optionally be configured such that the processor can control configuration of the second capacitor to be in series with the first capacitor, during delivery of the first electrostimulation voltage from the first capacitor to the target, in response to a disabling of an evoked response sensing mode.

In Example 13, the apparatus of one or more of Examples 12-13 can optionally be configured such that the processor can be configured to control a substantial discharging of the second capacitor after the delivery of the first electrostimulation voltage.

In Example 14, the apparatus of one or more of Examples 12-14 can optionally be configured such that a capacitance of the second capacitor is configurable between different at least first and second capacitance values. The processor can include an evoked-response sensing mode. The processor can be configured to place the second capacitor in series with the first capacitor during delivery of the first electrostimulation voltage to an electrostimulation target, such that the first capacitance value is used during the delivery when in an evoked-response sensing mode and the second capacitance value is used during the delivery when not in an evoked-response sensing mode.

Example 15 describes a method. In this example, the method can comprise generating a first electrostimulation voltage and storing the first electrostimulation voltage in a first capacitor disposed in a first electrostimulation energy delivery channel, and borrowing a second capacitor from a second electrostimulation energy delivery channel, during delivery of the first electrostimulation voltage to a target, for assisting the delivery of the first electrostimulation voltage to the target.

In Example 16, the method of Example 15 can optionally comprise configuring the second capacitor to be in series with the first capacitor during delivery of the first electrostimulation voltage from the first capacitor to the target.

In Example 17, the method of any one or more of Examples 15-16 can optionally comprise substantially discharging the second capacitor after the delivery of the first electrostimulation voltage from the first capacitor to the target.

In Example 18, the method of any one or more of Examples 15-17 can optionally be performed such that borrowing the second capacitor includes borrowing the second capacitor when an auto-threshold mode is disabled.

In Example 19, the method of any one or more of Examples 15-18 can optionally comprise using a backup pacing capacitor to operate as a coupling capacitor when an evoked response sensing mode is disabled.

In Example 20, the method of any one or more of Examples 15-19 can optionally comprise using a backup pacing capacitor to operate as a coupling capacitor when an autothreshold mode is disabled.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
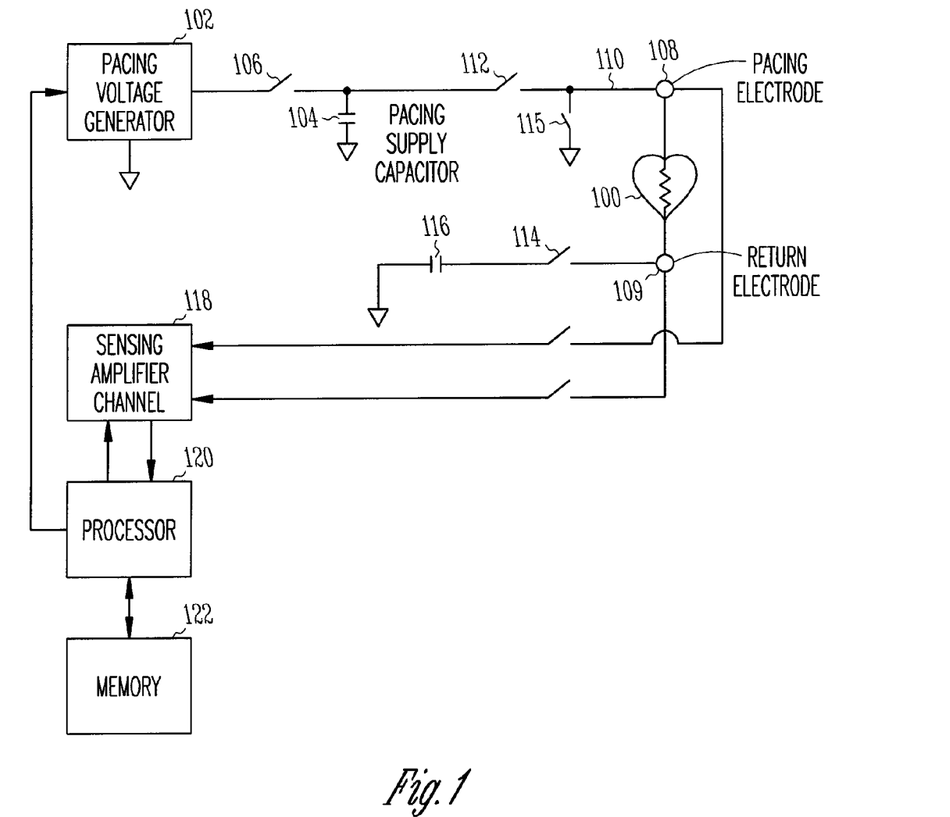
FIG. 1 shows an example of portions of an implantable cardiac rhythm management device, such as for delivering paces to, or sensing spontaneous intrinsic or evoked intrinsic depolarizations from a desired portion of a heart.

FIG. 1 shows an example of a portions of an implantable cardiac rhythm management device, such as for delivering paces to, or sensing spontaneous intrinsic or evoked intrinsic depolarizations from, a desired portion of a heart 100. Spontaneous intrinsic depolarizations are generated by the heart itself, while evoked intrinsic depolarizations are the result of an electrostimulation pulse such as a pacing pulse. Depolarization of a heart chamber causes it to contract. After contraction, while the heart chamber is expanding to fill with blood, repolarization occurs.

FIG. 1 illustrates an example of a pacing voltage generator 102, which generates a regulatable voltage that is stored on a pacing supply capacitor 104. A switch 106 can be used to selectively couple or decouple the pacing voltage generator 102 to or from the supply capacitor 104. A pace pulse can be delivered to the heart 100, such as via electrodes 108 and 109 (e.g., on a lead 110, in certain examples), such as by closing switches 112 and 114. In this example, during delivery of the pacing pulse, a coupling capacitor 116 is included in the return path from the electrode 109 to ground. Alternatively, the coupling capacitor 116 can be configured in series between the pacing supply capacitor 104 and the pacing electrode 108 (not shown). After non-zero delay period following the delivery of the pacing pulse, such as during the repolarization of the heart, a "recharge" period can be initiated. During the recharge period, switch 112 is opened and switches 114 and 115 can be closed to bleed the voltage accumulated during the pace pulse from the coupling capacitor 116 back toward zero.

Figure 2:
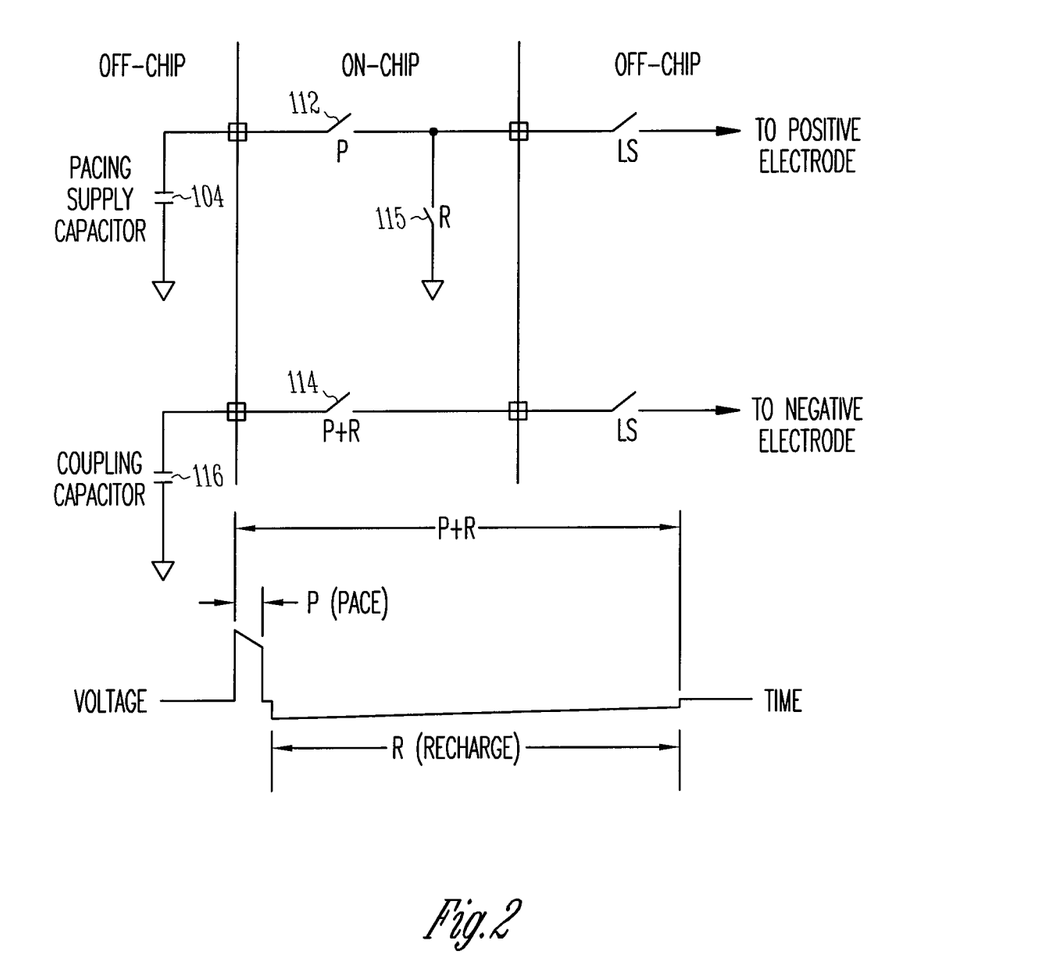
FIG. 2 shows an example of a pacing and recharge pulse, along with an example capacitor and switching configuration.

FIG. 2 shows an example of the voltage waveform between the electrodes 108 and 109 during "pacing" and "recharge" periods "P" and "R," respectively, along with another illustration of the switching configuration, which additionally includes off-chip lead switches "LS" that are ordinarily "on" except during internal or external defibrillation shocks. (Note: The "LS" lead switch may not be present in a bradycardia pacer device, depending on the input protection scheme employed). During a pacing period "P", the switches 112 and 114 are closed. During the recharge period "R," the switches 114 and 115 are closed.

In the example of FIGS. 1 and 2, spontaneous or evoked intrinsic depolarizations can also be sensed, such as between the electrodes 108 and 109, via a sensing amplifier channel 118 (which can include a sensing amplifier as well as other signal processing components). The resulting sensed information can be provided to a processor 120, such as for further processing. In this example, the processor 120 can access an onboard or separate memory 122, such as for reading or storing information. The processor 120 can also control operation of other components, such as the pacing voltage generator 102, the switches 106, 112, 114, and 115, the sensing amplifier channel 118, or the memory 122.

In an auto-threshold mode, the implantable device can cycle through various pacing output energies, such as by varying the voltage stored on the pacing supply capacitor 104, or by varying the pacing pulsewidth time, during which energy stored on the pacing supply capacitor 104 is coupled to the pacing electrode 108. By automatically determining the delivered "threshold" energy below which a responsive depolarization is no longer evoked, the pacing output energy can be automatically or manually set to be above that threshold value, such as by a desired safety margin. Similarly, in an auto-capture mode, the implantable device can automatically sense, such as following a delivered pace, to determine whether the delivered pace resulted in a responsive evoked depolarization. The pacing output energy can be automatically adjusted, such as to be above that threshold value, either for a prolonged period of time, or on a beat-to-beat basis.

Thus, auto-capture and atrial auto-threshold can both involve sensing an evoked response from the heart shortly after the delivery of a pacing pulse. A potential challenge to achieving reliable sensing or detection of the evoked response signal is a pace pulse lead polarization (e.g., "afterpotential") artifact as seen across the electrodes 108 and 109 directly following a pace/recharge event. In certain examples in which an electrode configuration of the device includes additional electrodes other than electrodes 108 and 109 (such as an additional right ventricular coil electrode and an additional right atrial coil electrode, in a defibrillator device), any evoked response can be sensed using such other electrodes— since such other electrodes are different from those used to deliver the pace pulse, they can quickly sense the evoked response without being affected by the afterpotential seen at the electrodes 108 and 109. Such a scheme results in little or no pace artifact seen on the evoked response sensing channel.

However, certain bradycardia devices may not have available leads with such separate electrodes to allow such sensing of the evoked response to be independent from the electrodes used to deliver the pacing pulse. In such configurations, evoked response sensing could potentially be affected by such pacing artifacts. The present inventors have recognized, among other things, that one way to reduce or this artifact is to reduce the capacitance of the coupling capacitor 116, such as during such evoked response sensing. Examples of evoked response sensing are described in U.S. Pat. Nos. 6,226,551, 6,427,085, and 5,941,903, each of which is incorporated by reference herein in its entirety, including its description of evoked response detection. As an illustrative example, the pace artifact during evoked response sensing can be reduced by using a smaller (e.g., 2.2 µF) coupling capacitor 116 during evoked response sensing, and using a larger (e.g., 10 µF) coupling capacitor 116 during non-evoked response pacing.

While providing better sensing visibility of the evoked response signal, however, the smaller coupling capacitor value can also alter the shape of the pacing waveform. For example, a smaller coupling capacitor generally results in a faster decay in pacing pulse amplitude, since the voltage drop between the leading edge amplitude and the trailing edge amplitude is a function of the RC time constant formed by the pacing supply capacitor 104, the coupling capacitor 116, and the series resistance of the heart load and transistor switches. Thus, using a smaller coupling capacitor value can decrease the trailing edge amplitude of the pace pulse, which, in turn, can effectively limit the usable pacing pulsewidth duration. The present inventors have recognized that one solution is to have both a smaller (e.g., 2.2 µF) coupling capacitor 116 and a larger (e.g., 10 µF) coupling capacitor available, and to automatically use the smaller coupling capacitor 116 during evoked response sensing (such as during auto-threshold, auto-capture, or both), and to automatically otherwise use the larger coupling capacitor 116. The present inventors have also recognized that, in a size-constrained implantable device, it is possible to use a switching configuration that "borrows" a coupling capacitor from another pacing channel, such as described further below.

Figure 3:
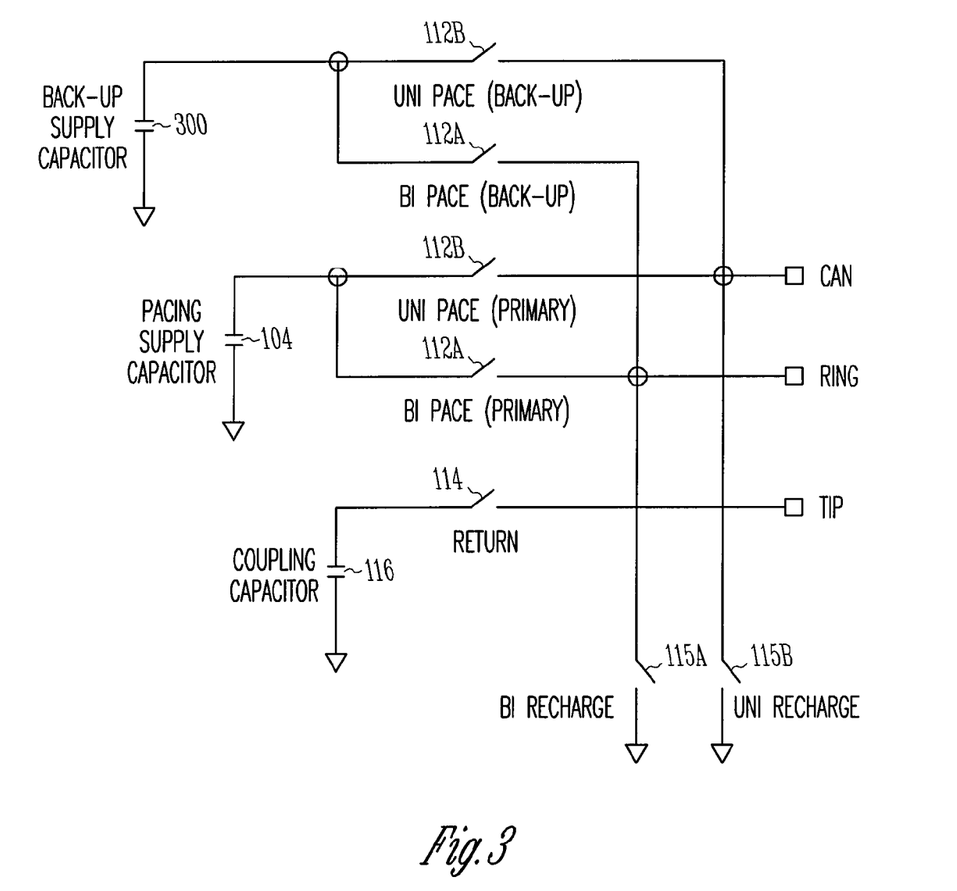
FIG. 3 shows an example of a pacing channel that can be used in a device with multiple pacing channels.

FIG. 3 is a block diagram illustrating generally an example of a switching configuration for a particular pacing channel, where the particular pacing channel can be associated with a particular location of the heart to which the pacing energy is to be delivered. In an example, multiple pacing channels can be individually associated with different locations of the heart to which the pacing energy is to be delivered. As an illustrative example, a single-chamber pacing to a right ventricle (RV) can use a single pacing channel, such as shown in FIG. 3. As another illustrative example, dual-chamber pacing to a RV and a right atrium (RA) can use two such pacing channels. As a further illustrative example, tri-chamber pacing to a RA, a RV, and a left ventricle (LV) can use three pacing channels. Other configurations or more pacing channels are also possible.

In the example of FIG. 3, in addition to the pacing supply capacitor 104 and the return coupling capacitor 116, a back-up pacing supply capacitor 300 is also included in a particular pacing channel. In this example, each of the normal pacing supply capacitor 104 and the back-up pacing supply capacitor can include separate respective switches 112A and 112B, such as for respectively coupling to a ring electrode during bipolar pacing pulse delivery, and to a "can" electrode (associated with a housing of the implantable device) during unipolar pacing pulse delivery.

In an example in which multiple such pacing channels are used, the back-up pacing capacitor 300 from another pacing channel can be "borrowed" by a particular pacing channel for use as its coupling capacitor 116, such as when auto-capture is not enabled. Indeed, even in a single chamber pacing device with an auto-threshold backup pacing supply, the backup pacing supply capacitor can be interchanged with the coupling capacitor (e.g., when not operating in the auto-threshold mode) to provide wider pace pulses. In an illustrative example, suppose that an implantable device includes separate RA, RV, and LV pacing channels, each including: a 10 µF pacing supply capacitor 104, a 2.2 µF coupling capacitor 116, and a 10 µF back-up pacing supply capacitor 300. Except when RV autocapture is enabled, the RV pacing channel can use the RA channel's 10 µF backup pacing supply capacitor 300 as its coupling capacitor 116. When RV autocapture is enabled, the RV pacing channel uses its own 2.2 µF coupling capacitor 116, rather than borrowing from another channel. In this example, the "borrowing" of the back-up supply capacitor 300 from another channel can involve closing a switch (not shown) between the capacitor 300 and the TIP electrode, instead of switch 114.

In another example, a particular pacing channel can borrow its own back-up pacing capacitor 300 for use as the coupling capacitor 116, rather than borrowing from another pacing channel. However, in such an example, back-up pacing for that channel is unavailable, since that channel's own backup pacing capacitor 300 is being used as the coupling capacitor 116.

In yet another example, a particular pacing channel can borrow another pacing channel's coupling capacitor 116 for use as its coupling capacitor 116, rather than borrowing a back-up pacing supply capacitor from another pacing channel.

Table 1 below lists an illustrative example of various configurations of capacitors used for the coupling capacitor 116 in an embodiment in which there are three pacing channels: an RV pacing channel, an RA pacing channel, and an LV pacing channel. Three "control bits" are coded to select a particular configuration from the eight available in this example.

TABLE 1

Coupling Capacitor Configurations

| Control Bits | Cap Used for RA Coupling Cap | Cap Used for RV Coupling Cap | Cap Used for LV Coupling Cap |
|---|---|---|---|
| 000 | RA coupling cap 116 | RV coupling cap 116 | LV coupling cap 116 |
| 001 | RA coupling cap 116 | RV backup cap 300 | LV coupling cap 116 |
| 010 | RV coupling cap 116 | RA coupling cap 116 | LV coupling cap 116 |
| 011 | RA coupling cap 116 | LV coupling cap 116 | RV coupling cap 116 |
| 100 | RA coupling cap 116 | RV coupling cap 116 | LV coupling cap 116 |
| 101 | RA coupling cap 116 | RV coupling cap 116 | LV coupling cap 116 |
| 110 | RV coupling cap 116 | RA coupling cap 116 | LV coupling cap 116 |
| 111 | RV coupling cap 116 | RA coupling cap 116 | LV coupling cap 116 |

Figure 4:
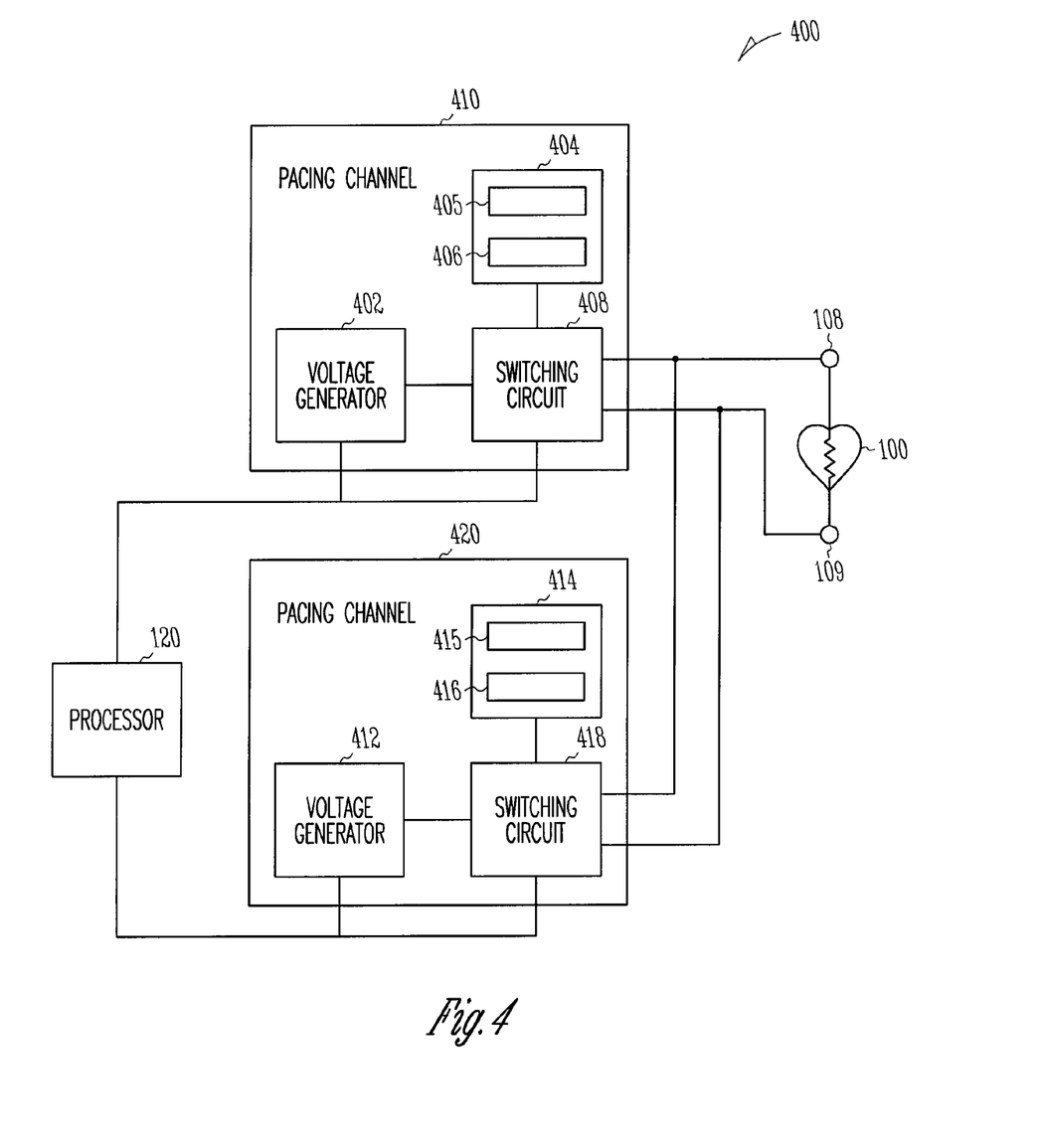
FIG. 4 shows an example of a system for delivering electrostimulation to a desired portion of the heart.

FIG. 4 shows an example of an apparatus 400 that can be used for delivering one or more electrostimulations to a target. In an example, the apparatus 400 can be coupled to a heart 100, such as by using electrodes 108 and 109. In an example, an implantable medical device 401 can include a first electrostimulation delivery channel 410, a second electrostimulation delivery channel 420, a processor 120, and electrodes 108 and 109 that can be coupled to the heart 100.

In an example, the first electrostimulation channel 410 can include a voltage generator 402, a capacitor module 404, and a switching circuit 408. In an example, the capacitor module 404 can include a pacing supply capacitor 405 and can include a return or other coupling capacitor 406.

In an example, the second electrostimulation channel 420 can include a voltage generator 412, a capacitor module 414, and a switching circuit 418. In an example, the capacitor module 414 can include a pacing supply capacitor 415 and can include a return or other coupling capacitor 416.

In an example, the voltage generator 402 can be coupled to the switching circuit 408. In an example, the capacitor module 404 can be coupled to the switching circuit 408, which, in turn, can be coupled to electrodes 108 and 109, which can be located in association with the heart 100. In an example, the voltage generator 402 can be configured to generate an electrostimulation voltage and provide the electrostimulation voltage to the capacitor module 404, such as by activating the switching circuit 408, or otherwise. In an example, the capacitor module 404 stores the electrostimulation voltage on the pacing supply capacitor 405. In an example, the switching circuit 408 can be used to selectively engage the capacitor module 404, such as during delivery of the electrostimulation to a desired portion of the heart 100.

In an example, the voltage generator 412 can be coupled to the switching circuit 418. In an example, the capacitor module 414 can be coupled to the switching circuit 418, which, in turn, can be coupled to electrodes 108 and 109. In an example, the voltage generator 412 can be configured to generate an electrostimulation voltage and to provide the electrostimulation voltage to the capacitor module 414 such as by activating the switching circuit 418. In an example, the capacitor module 414 can store the electrostimulation voltage across the pacing supply capacitor 415. In an example, the switching circuit 418 can be configured to selectively engage the capacitor module 414, such as during the delivery of the electrostimulation voltage to a desired portion of the heart 100.

In an example, the processor 120 is coupled to the voltage generators 402, 412 and the switching circuits 408, 418. In an example, the processor 120 is configured to control the switching circuits 408, 418. In an example, the processor 120 can configure one of the capacitors 415, 416 in the capacitor module 414 to be in series with the pacing supply capacitor 405 such as during delivery of an electrostimulation voltage from the pacing supply capacitor 405 to a target portion of the heart 100.

In an example, at least one of first electrostimulation channel 410 and second electrostimulation channel 420 can include a single pacing channel for single-chamber pacing to a right ventricle (RV). In another example, at least one of first electrostimulation channel 410 and second electrostimulation channel 420 can include two pacing channels for dual-chamber pacing to a RV and a right atrium (RA). In yet another example, at least one of first electrostimulation channel 410 and second electrostimulation channel 420 can include three pacing channels for tri-chamber pacing to a RA, a RV, and a left ventricle (LV). Other configurations using more pacing channels are also possible.

In the example of FIG. 4, switching circuit 408 can be configured to couple the pacing supply capacitor to a ring electrode, such as during bipolar pacing pulse delivery and to a "can" electrode (e.g., associated with a housing or attached header of an electronics unit of the implantable device), such as during unipolar pacing pulse delivery.

In operation, the apparatus 400 can be configured such that a particular channel can borrow a capacitor (e.g., the pacing capacitor 414, the back-up capacitor, or the return coupling capacitor 416) from an alternate channel during the particular channel's delivery of electrostimulation voltage to the heart 100. In an example, the capacitor is borrowed from the capacitor module 414 during delivery of an electrostimulation voltage stored in the capacitor module 404 to a desired portion of the heart 100, when an auto-capture or an auto-threshold mode is disenabled. In an example, this borrowing can be triggering such disabling of auto-capture mode, auto-threshold mode, or other evoked-response sensing mode. In an example, the "borrowing" of the back-up capacitor from the capacitor module 414 from the second electrostimulation channel 420 can involve closing at least one or more of the switching circuits 408 or 418.

In an example, the second electrostimulation channel 420 can be configured as an alternate electrostimulation channel. In an example, a particular pacing channel 410 (e.g., RA pacing channel) can borrow its own back-up pacing capacitor 415 for use as or with its coupling capacitor 406, such as to modify the effective value of the coupling capacitor 406 during electrostimulation, rather than borrowing a capacitor from another pacing channel (e.g., RV pacing channel). However, in such an example, back-up pacing for the particular pacing channel 410 can be rendered unavailable, since that particular pacing channel's own backup pacing capacitor 415 is being used as the coupling capacitor 406.

In yet another example, a particular pacing channel 410 (e.g., RA pacing channel) can borrow a coupling capacitor 416 of another pacing channel 420 (e.g., RV pacing) for use as its coupling capacitor 406, rather than borrowing a back-up pacing supply capacitor 415 from the other pacing channel 420 (e.g. the RV pacing channel).

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   an implantable medical device, comprising:
   a first electrostimulation voltage generator, configured to generate a first electrostimulation voltage;
   a first capacitor having a first capacitance value, coupled to the first electrostimulation voltage generator, and configured to be capable of storing the first electrostimulation voltage;
   a second capacitor having a second capacitance value; and
   a third capacitor having a third capacitance value, wherein the third capacitance value exceeds the second capacitance value; and
   a processor, comprising an evoked-response sensing mode, the processor configured to place one of the second capacitor and the third capacitor in series with the first capacitor during delivery of the first electrostimulation voltage to an electrostimulation target, such that the second capacitor is used during the delivery when in an evoked-response sensing mode and the third capacitor is used during the delivery when not in an evoked-response sensing mode,
   wherein the evoked-response sensing mode comprises at least one of an autocapture mode or an autothreshold mode
   wherein the first electrostimulation voltage generator and the first capacitor are arranged in a first pacing channel,
   wherein the third capacitor comprises a capacitor from a different pacing channel when the evoked-response sensing mode is enabled, and
   wherein the processor is configured to switch from the second capacitance value to the third capacitance value by substituting the third capacitor for use as the second capacitor when the evoked-response sensing mode is enabled.

2. The apparatus of claim 1, further comprising:
   a first switching circuit, coupled to the first capacitor, configured to facilitate delivery of the first electrostimulation voltage from the first capacitor to a target.

3. The apparatus of claim 1, further comprising:
   a second electrostimulation voltage generator, configured to generate a second electrostimulation voltage, wherein the third capacitor is configured to be capable of storing the second electrostimulation voltage.

4. The apparatus of claim 3, further comprising
   a second switching circuit, coupled to the third capacitor, configured to facilitate delivery of the second electrostimulation voltage from the second capacitor to a target.

5. The apparatus of claim 1, wherein the processor is configured to control configuration of the third capacitor to be in series with the first capacitor during delivery of the first electrostimulation voltage from the first capacitor to a target.

6. The apparatus of claim 5, wherein the processor is configured to control configuration of the third capacitor to be in series with the first capacitor, during delivery of the first electrostimulation voltage from the first capacitor to the target, in response to a disabling of the evoked response sensing mode.

7. The apparatus of claim 1, wherein the processor is configured to control a substantial discharging of the third capacitor after the delivery of the first electrostimulation voltage to a target.

8. The apparatus of claim 1, wherein the second capacitor is configured to operate as a decoupling capacitor, and wherein the second capacitor has a value of about 2.2 microfarads.

9. The apparatus of claim 1, wherein the substituted third capacitor that is used as the second capacitor when the evoked-response sensing mode is enabled is configured to operate as a decoupling capacitor.

10. The apparatus of claim 1, wherein the second capacitor comprises a capacitor from a different pacing channel.

\* \* \* \* \*

UNITED STATES PATENT AND TRADEMARK OFFICE
CERTIFICATE OF CORRECTION

PATENT NO. : 8,694,095 B2  
APPLICATION NO. : 12/328603  
DATED : April 8, 2014  
INVENTOR(S) : Lyden et al.

Page 1 of 1

It is certified that error appears in the above-identified patent and that said Letters Patent is hereby corrected as shown below:

In the Claims:

In column 10, line 38, in Claim 1, after "mode", insert --,--, therefor

In column 10, line 43, in Claim 1, before "enabled,", insert --not--, therefor

In column 10, line 48, in Claim 1, before "enabled.", insert --not--, therefor

Signed and Sealed this  
Twenty-first Day of October, 2014

Michelle K. Lee  
*Deputy Director of the United States Patent and Trademark Office*